United States Patent
Sato et al.

(10) Patent No.: US 11,479,751 B2
(45) Date of Patent: Oct. 25, 2022

(54) DRIED POWDER OF MICROORGANISMS AND METHOD FOR PRODUCING SAME

(71) Applicant: Nippon Suisan Kaisha, Ltd., Tokyo (JP)

(72) Inventors: Seizo Sato, Tokyo (JP); Takayoshi Sekiguchi, Tokyo (JP); Yuko Ishiwata, Tokyo (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 208 days.

(21) Appl. No.: 16/966,188

(22) PCT Filed: Jan. 31, 2019

(86) PCT No.: PCT/JP2019/003510
§ 371 (c)(1),
(2) Date: Jul. 30, 2020

(87) PCT Pub. No.: WO2019/151452
PCT Pub. Date: Aug. 8, 2019

(65) Prior Publication Data
US 2021/0040439 A1    Feb. 11, 2021

(30) Foreign Application Priority Data
Jan. 31, 2018    (JP) .............................. JP2018-015194

(51) Int. Cl.
| | | |
|---|---|---|
| *C12N 1/12* | (2006.01) | |
| *A23L 5/46* | (2016.01) | |
| *A23L 33/115* | (2016.01) | |
| *A61K 8/99* | (2017.01) | |

(52) U.S. Cl.
CPC .................. *C12N 1/12* (2013.01); *A23L 5/46* (2016.08); *A23L 33/115* (2016.08); *A61K 8/99* (2013.01)

(58) Field of Classification Search
CPC ...................................................... C12N 1/12
See application file for complete search history.

(56) References Cited

U.S. PATENT DOCUMENTS

| | | |
|---|---|---|
| 2016/0177255 A1 | 6/2016 | Radakovits et al. |
| 2017/0016036 A1 | 1/2017 | Calleja et al. |

FOREIGN PATENT DOCUMENTS

| | | |
|---|---|---|
| JP | H03-504676 A | 10/1991 |
| JP | 2013-053089 A | 3/2013 |
| JP | 2014-508136 A | 4/2014 |
| JP | 2016-127809 A | 7/2016 |
| WO | WO-89/09278 A1 | 10/1989 |
| WO | WO-2012/100991 A1 | 8/2012 |
| WO | WO-2013/054812 A1 | 4/2013 |

OTHER PUBLICATIONS

English machine translation of Kan et al., CN 105026549 A, 2015.*
Kang, Dong-Hoon et al., "Effect of salt concentration on production of polyunsaturated fatty acids in *Thraustochytrium aureum* ATCC 34304," Korean J. Chem. Eng., 2007, vol. 24, No. 4, p. 651-654.
Singh, A. et al., "Docosahexaenoic acid (DHA) production by *Thraustochytrium* sp. ATCC 20892," World Journal of Mictobioligy & Biotechnology, 1996, vol. 12, p. 76-81.
International Search Report dated Apr. 16, 2019 for PCT/JP2019/003510.
Ueda, Mayumi et al., "Seasonal dynamics of culturable thraustochytrids (Labyrinthulomycetes, Stramenopiles) in estuarine and coastal waters," Aquatic Microbial Ecology 2015, vol. 74, pp. 187-204.
Extended European Search Report dated Sep. 24, 2021 in European Patent Application No. 19747005.7.

* cited by examiner

*Primary Examiner* — Rosanne Kosson
(74) *Attorney, Agent, or Firm* — BannerWitcoff, Ltd.

(57) ABSTRACT

Provided is a dried powder of microorganisms, which is highly suitable for processing and has excellent usefulness as one component of various products. The present invention provides: a dried powder of microorganisms, the dried powder exhibiting a brightness of 55 or more and a chromaticness of 18 or less; and a method for producing a dried powder of microorganisms, the method comprising: washing microorganisms at least once with a liquid having an osmotic pressure lower than that of a liquid culture medium for culturing the microorganisms; and drying and heating the microorganisms after the washing to thereby obtain the dried powder of the microorganisms, which exhibits a brightness of 55 or more and a chromaticness of 18 or less.

12 Claims, No Drawings

DRIED POWDER OF MICROORGANISMS AND METHOD FOR PRODUCING SAME

CROSS REFERENCES TO RELATED APPLICATIONS

This application is the National Stage of International Application No. PCT/JP2019/003510 filed Jan. 31, 2019, and claims benefit of Japanese Application No. 2018-015194 filed on Jan. 31, 2018.

FIELD

The present disclosure relates to a dry powder of microorganisms and a method of producing the dry powder of microorganisms.

BACKGROUND

Since ancient times, it has been known that certain microorganisms contain many useful components, and these useful components have been utilized in various applications. Useful components derived from microorganisms are utilized as isolated components extracted or separated from microorganisms, and in addition, those may be utilized as components within microorganisms, not as isolated components. An example of the form utilized as components within microorganisms includes a dry powder of microorganisms.

The dry powder of microorganisms can be obtained by drying microorganisms themselves as they are. Dry-powdered microorganisms can be utilized as they are in applications according to their useful component in the microorganisms and widely used as a component of various products, such as, for example, cosmetics, food and beverage products, and pharmaceuticals.

Dry-powdered microorganisms, that is, dry powders of microorganisms, have advantages, such as superior storage properties and superior handling properties. In addition, a dry powder of microorganisms can be easily mixed with other components in a liquid form, or a solid form such as powder, and thus has an advantage of superior processing properties. Therefore, in order to effectively utilize the useful components that organisms, not limited to microorganisms, have, various dry powders obtained by powdering whole organisms themselves have been proposed.

For example, Patent Document 1 discloses a powdered brown alga containing a water-soluble algin and an insoluble component, and a suspending agent or a food-product improvement agent containing this powdered brown alga. Patent Document 1 describes that the powdered brown alga according to Patent Document 1 is obtained by pulverizing, washing, and drying brown algae, and has an L value of not less than 45 which indicates the lightness of a color. In addition, Patent Document 1 discloses mixing the food-product improvement agent containing this powdered brown alga with other raw materials to produce a food product, such as bread and gelled food.

CITATION LIST

Patent Literature

Patent Document 1: WO 2013/054812

SUMMARY

Technical Problem

However, in utilizing a dry powder of microorganisms as a component of a product, such as a food product, a dry powder having a low-lightness color or a high-chroma color may impair an impression of the color of the product. Such a dry powder having a low-lightness color or a high-chroma color is often found in dry powders obtained from microorganisms, such as those after culturing, and, in particular, dry powders of microorganisms, the dry powders that have undergone heat sterilization. A dry powder having such a color may have impaired the impression of the color of a product when used as a component of the product, such as a food product.

Thus, such a dry powder having a low-lightness or high-chroma color is difficult to utilize as a component in products with high preference for color, such as, for example, food and beverage products, personal care products, pharmaceuticals, quasi drugs, and animal feeds, and thus has inferior processing suitability.

Thus, an object of the present disclosure is to provide a dry powder of microorganisms having superior processing suitability and excellent utility as a component of various products.

Solution to Problem

The present disclosure includes the following.

(1) A dry powder of microorganisms having a lightness of not less than 55 and a chroma of not greater than 18.

(2) The dry powder according to (1), having a lightness of not less than 58 and a chroma of not greater than 18.

(3) The dry powder according to (1), having a lightness of not less than 58 and a chroma of not greater than 17.

(4) The dry powder according to (1), having a lightness of not less than 60 and a chroma of not greater than 15.

(5) The dry powder according to any one of (1) to (4), wherein the microorganisms are oil/lipid-producing microorganisms.

(6) The dry powder according to any one of (1) to (5), wherein the microorganisms are at least one species of microorganisms selected from the group consisting of microorganisms belonging to *Stramenopiles*.

(7) The dry powder according to any one of (1) to (6), wherein the microorganisms are at least one species of microorganisms selected from the group consisting of microorganisms belonging to *Labyrinthulea*.

(8) A dry powder production method of producing a dry powder of microorganisms, the method including: washing microorganisms at least once using a liquid having a lower osmotic pressure than a liquid medium for culturing the microorganisms; and heating and drying the microorganisms after the washing to obtain a dry powder of microorganisms, the dry powder having a lightness of not less than 55 and a chroma of not greater than 18.

(9) The production method according to (8), further including an autoclaving step.

(10) The production method according to (9), including the autoclaving step after the washing.

(11) The production method according to any one of (8) to (10), wherein the washing is performed one to three times.

(12) The production method according to any one of (8) to (11), wherein the microorganisms are microorganisms after culturing, and the method further includes a culturing step for culturing microorganisms before the washing.

(13) The production method according to any one of (8) to (12), wherein the microorganisms are oil/lipid-producing microorganisms.

(14) A powder product containing the dry powder described in any one of (1) to (7).

(15) A method of producing a microbial-derived component-containing composition, the method including: preparing the dry powder described in any one of (1) to (7); and obtaining a microbial-derived component-containing composition from the prepared dry powder.

(16) A microbial-derived component-containing composition obtained by the method according to (15).

Advantageous Effects of Invention

The present disclosure can provide a dry powder of microorganisms, the dry powder having superior processing suitability and excellent utility as a component of various products.

DESCRIPTION OF EMBODIMENTS

A dry powder of the present disclosure is a dry powder of microorganisms, the dry powder having a lightness of not less than 55 and a chroma of not greater than 18.

A method of producing a dry powder of the present disclosure is a production method including: washing microorganisms at least once using a liquid having a lower osmotic pressure than a liquid medium for culturing the microorganisms; and heating and drying the microorganisms after the washing to obtain a dry powder of microorganisms, the dry powder having a lightness of not less than 55 and a chroma of not greater than 18.

The present disclosure provides a dry powder of microorganisms, the dry powder having a lightness of not less than 55 and a chroma of not greater than 18, in other words, a microbial dry powder being bright and having an achromatic color, and thus can provide a dry powder of microorganisms, the dry powder with superior processing suitability and excellent utility as a component of various products.

To explain this further, the present disclosure is based on the finding that the lightness and chroma of the microbial dry powder can be easily adjusted in the production process of the microbial dry powder. The bright and achromatic microbial dry powder gives a good impression, and is less likely to impair the overall color impression of the product when combined with other components in producing a particular product. Thus, the subject dry powder is a dry powder of microorganisms having excellent utility, and is easily utilized as a component of a wide range of products, such as food and beverage products, personal care products, pharmaceuticals, quasi drugs, and animal feeds, that is, having superior processing suitability.

In the present specification, the term "step" includes not only an independent step but also a step that cannot be clearly distinguished from other steps provided that an intended purpose of the step is achieved.

In the present specification, numerical ranges indicated by "to" are ranges including the numerical values described before and after the "to" as the minimum and maximum values, respectively.

In the present specification, when a plurality of substances corresponding to each component is present in a mixture, the amount or content ratio of each component in the mixture means the total amount or content of the plurality of substances present in the mixture, unless otherwise noted. In the present specification, the term "not greater than" or "less than" with regard to a percentage includes 0%, that is, "not containing", or means a range including a value undetectable by present means, unless the lower limit value is specifically stated.

The term "effective amount" used in the present specification refers to an amount of a composition sufficient to provide a beneficial result or a desired result. The effective amount can be administered in one or more administrations, applications, or dosages, or can be optionally combined with another substance, and can be defined as an amount not limited to a particular formulation or route of administration.

Hereinafter, the present disclosure will be described.

Dry Powder

The dry powder according to the present disclosure is a dry powder of microorganisms and has a lightness of not less than 55 and a chroma of not greater than 18.

In the present specification, the "dry powder of microorganisms" refers to a product powdered by subjecting microbial cells to a predetermined drying method.

The lightness and chroma of the dry powder mean values measured with a chroma meter, in particular, values measured with a chroma meter according to the LCh color system. The chroma meter is not particularly limited, and, for example, a chroma meter "CR-300" (Konica Minolta Japan, Inc.) can be used. The measurement can be made according to the product instruction manual. Specifically, the dry powder is arranged at a certain size, for example, a size having a particle diameter of not more than 1 mm, and at a certain thickness, and white calibration is performed with a white calibration plate, thereafter the measurement is made by applying the measuring head part perpendicular to the sample. At this time, the measurement is made at a temperature condition of 15° C. to 30° C. with a relative humidity of not more than 30% to prevent the drastic change in the water content of the dry powder.

Lightness in the LCh color system has a range from 0 to 100. For the lightness, 0 is the lowest value indicating the darkest state, that is, full black color, and 100 is the highest value indicating the brightest state, that is, the full white color. The chroma in the LCh color system has a range from 0 to 60. For the chroma, 60 is the highest value indicating the most brilliant state, and 0 is the lowest value indicating the dullest state.

The lightness of the dry powder can be not less than 55, and as the value of the lightness increases, the lightness increases. For example, the lightness in the dry powder may be not less than 58, not less than 60, not less than 62, not less than 64, or not less than 65. The upper limit value of the lightness is not particularly limited. In one embodiment of the present disclosure, the upper limit value of the lightness can be, for example, not greater than 70 or not greater than 68 in terms of harmony with the colors of other formulation components.

The chroma of the dry powder can be not greater than 19, and as the chroma value decreases, the color gets closer to an achromatic color (black, white, gray). For example, the chroma in the dry powder may be not greater than 18, not greater than 17, not greater than 16, not greater than 15, or not greater than 14. The lower limit value of the chroma is not particularly limited. In one embodiment of the present disclosure, the lower limit value of the chroma can be, for example, not less than 1 or not less than 5 in terms of harmony with the color spaces or vividness of the colors of other formulation components.

A dry powder satisfying both lightness and chroma as described above can exhibit a relatively strong impression of a bright and achromatic color, provides a good impression, and also has excellent processing suitability.

The hue of the dry powder is not particularly limited. The hue of the dry powder is often dependent on the color inherent in the microbial cells constituting the dry powder.

The hue of the dry powder can be, for example, from 55 to 120, from 60 to 110, or from 70 to 90.

The lightness and chroma in the dry powder may be any combination of the lightness and chroma described above, for example, each embodiment of the present disclosure includes any dry powder of the following:

(1) a dry powder having a lightness of not less than 58 and a chroma of not greater than 18, (2) a dry powder having a lightness of not less than 58 and a chroma of not greater than 17, (3) a dry powder having a lightness of not less than 60 and a chroma of not greater than 15, and (4) a dry powder having a lightness of not less than 55 and a chroma of not greater than 18.

The lightness of (1) to (4) above can be each not greater than 70, and the chroma of (1) to (4) above can be not less than 1 independently of or in combination with the above lightness.

The dry powders of (1) to (4) above are all bright and achromatic dry powders. Other embodiments of the present disclosure may have a different combination of the lightness and chroma other than (1) to (4).

The lightness, chroma, and hue measured with a chroma meter according to the LCh color space can be converted into another color space, La*b* color space.

Microorganisms that can provide the dry powder according to the present disclosure are not particularly limited and any microorganisms having a useful component within the microorganisms. The microorganisms can be microorganisms which are able to be cultured and may be any microorganisms obtained from natural collection or after culturing, as long as the microorganisms are able to be cultured. One species of these microorganisms may be used alone, or two or more species of them may be used in combination.

Examples of the applicable microorganisms may include at least one species selected from the group consisting of microorganisms belonging to fungi, microorganisms of green algae (*Chlorophycea*), microorganisms of *Euglena* algae (*Euglenida*), and microorganisms of SAR.

Examples of the fungi may include yeast and filamentous fungi. Examples of the yeast may include at least one species of microorganisms selected from the group consisting of microorganisms of the genus *Yarrowia*, microorganisms of the genus *Pichia*, microorganisms of the genus *Saccharomyces*, microorganisms of the genus *Cryptococcus*, and microorganisms of the genus *Trichosporn*. Examples of the filamentous fungi may include at least one species of microorganisms selected from the group consisting of microorganisms of the genus *Mortierella*, microorganisms of the genus *Pythium*, and microorganisms of the genus *Phytophthora*. Among them, the microorganisms belonging to the genus *Mortierella* are more preferred. Examples of the microorganisms belonging to the genus *Mortierella* may include *Mortierella elongata*, *Mortierella exigua*, *Mortierella hygrophila*, and *Mortierella alpina*.

Examples of the microorganisms of the green algae may include microorganisms belonging to the genus *Botryococcus, Pseudochoricystis, Scenedesmus*, and *Desmodesmus*.

Examples of the microorganisms of *Euglena* algae may include microorganisms belonging to the family *Euglenaceae*. Examples of the microorganisms belonging to the family *Euglenaceae* may include microorganisms belonging to the genus *Euglena*.

SAR means SPR in the classification system proposed by Adl et al. (Adl et. al., The Journal of Eukaryotic Microbiology. 59 (5): 429-493 (2012)), and specifically, microorganisms of *Stramenopiles*, *Alveolata*, and *Rhizaria* correspond. Among them, at least one species of microorganisms selected from the group consisting of microorganisms belonging to the *Stramenopiles* is preferred. Examples of the *Stramenopiles* may include at least one species of microorganisms selected from the group consisting of microorganisms of *Bicosoecida, Labyrinthulea, Blastocystis, Actinophyida, Opalinata, Placidida, Oomycetes, Hyphochytriomycetes, Developayella*, golden algae (*Chrysophyceae*), *Eustigmatophyceae, Phaeothamniophyceae, Pinguiophyceae, Raphidophyceae, Synurophyceae, Xantexyophyceae*, brown algae (*Phaeophyceae*), *Schizocladiophyceae, Chrysomerophyceae, Dictyochophyceae, Bolidophiceae, Pelagophyceae*, and diatoms (*Bacillariophyceae*).

Examples of the *Alveolata* may include microorganisms belonging to *Ciliophora, Apicomplexa*, and *Dinoflagellata*. Examples of the *Dinoflagellata* may include microorganisms belonging to the genus *Crypthecodinium*. Examples of the microorganisms belonging to the genus *Crypthecodinium* may include *Crypthecodinium cohnii*.

Among them, the microorganisms are preferably microorganisms belonging to *Labyrinthulea*, and among them, microorganisms belonging to the *Thraustochytrid* family are particularly preferred. The microorganisms belonging to the family *Thraustochytrid* are preferably, for example, microorganisms belonging to the genus *Aplanochytrium*, the genus *Japonochytrium*, the genus *Labyrinthuloides*, the genus *Schizochytrium*, the genus *Thraustochytrium*, the genus *Ulkenia*, the genus *Aurantiochytrium*, the genus *Oblongichytrium*, the genus *Botryochytrium*, the genus *Parietichytrium*, or the genus *Sicyoidochytrium*, and among them, particularly preferably, at least one species of microorganisms selected from the group consisting of microorganisms of the genus *Aurantiochytrium* can be selected.

The microorganisms described above are mainly microorganisms capable of producing oil/lipid and can be preferably applied as oil/lipid-producing microorganisms. In addition to the microorganisms described above, other microorganisms can be applied to provide the dry powder of the present disclosure, including microorganisms capable of producing things such as a polysaccharide, an antioxidant, a peptide, an amino acid, and a vitamin. Examples of such microorganisms may also include microorganisms capable of producing astaxanthin, such as microalgae including cyanobacteria, red algae, brown algae, green algae, diatoms, and *Eustigmatophyceae*, and in particular, microalgae belonging to the genus *Haematococcus*; and yeasts (e.g., *Phaffia* yeasts); microorganisms capable of producing a polysaccharide including microalgae belonging to the genera, such as *Euglena* and *Prasinococcus*; and filamentous fungi belonging to the genera, such as *Pestalotiopsis* and *Pestalotia*; black yeasts capable of producing pullulan; and yeasts capable of producing mannoprotein.

The microorganisms can have a useful component in the microbial cell. The useful component herein is not particularly limited and may be any component that can be produced in one microbial cell, and examples of the useful component may include amino acids, proteins, lipids, and vitamins. In one embodiment of the present disclosure, the microorganisms can be oil/lipid-producing microorganisms. In the present specification, an "oil/lipid" means a mixture of organic substances mainly composed of fatty acids and insoluble in water under normal temperature and normal pressure. Oil/lipids of microbial origin are referred to as "microbial oil/lipids" in the present specification. The microbial oil/lipids contain oily components, such as a saturated or unsaturated fatty acid, a phospholipid, a sterol, a glycerol, a ceramide, a sphingolipid, a terpenoid, a flavonoid, or a tocopherol, and the saturated or unsaturated fatty acid may also be present as a constituent fatty acid in another oily component.

In the present specification, the term "fatty acid" includes not only free saturated or unsaturated fatty acids themselves but also fatty acids contained as constituent units in free saturated or unsaturated fatty acids, saturated or unsaturated fatty acid alkyl esters, triglycerides, diglycerides, monoglycerides, phospholipids, steryl esters, and the like, and these fatty acids may be also called constituent fatty acids. In the present specification, unless otherwise noted, the forms of compounds containing fatty acids may be omitted. Examples of forms of compounds containing fatty acids may include a free fatty acid form, a fatty acid alkyl ester form, a glyceryl ester form, a phospholipid form, and a steryl ester form. Compounds containing the same fatty acids may be contained in a single form or may be contained as a mixture of two or more forms in the lipid.

Examples of the fatty acid as a useful component that can be contained in the microbial dry powder include unsaturated fatty acids, in particular, polyunsaturated fatty acids. "Highly polyunsaturated fatty acids" in the present specification means divalent or higher unsaturated fatty acids having at least 20 carbons. Examples of the polyunsaturated fatty acids having at least 20 carbons may include polyunsaturated fatty acids having from 20 to 22 carbons, specifically, eicosadienoic acid (C20:2, n–9, EDA), dihomo-γ-linolenic acid (C20:3, n–6, DGLA), Mead acid (C20:3, n–9, MA), eicosatetraenoic acid (C20:4, n–3, ETA), arachidonic acid (C20:4, n–6, ARA), eicosapentaenoic acid (C20:5, n–3, EPA), docosatetraenoic acid (C22:4, n–6, ETA), docosapentaenoic acid (C22:5, n–3, $_{n\text{-}3}$DPA), docosapentaenoic acid (C22:5, n–6, $_{n\text{-}6}$DPA), and docosahexaenoic acid (C22:6, n–3, DHA).

In addition, examples of other useful components that can be contained in the microbial dry powder may include polysaccharides, antioxidants, peptides, amino acids, vitamins, hydrocarbons, and compounds resulting from metabolism of any of these compounds, and the examples may also include carotenoids, xanthophylls, ubiquinones, isoprenoid-derived compounds, and compounds resulting from metabolism of any of these compounds.

The size of the dry microorganism powder is not particularly limited and can be appropriately set according to a method for crushing microorganisms in powdering or the like. The dry powder of microorganisms can typically have a particle diameter of 300 μm to 250 μm, 250 μm to 150 μm, or 150 μm to 20 μm. The particle diameter herein means a classification with a sieve. The particle diameter distribution of the dry powder of microorganisms is not particularly limited and can be appropriately set according to the type of the powdered microorganisms or the like.

Method of Producing Dry Powder

The method of producing a dry powder of microorganisms according to the present disclosure is a production method of producing a dry powder of microorganisms, the method including: washing microorganisms at least once using a liquid having a lower osmotic pressure than a liquid medium for culturing the microorganisms; and heating and drying the microorganisms after the washing to obtain a dry powder of microorganisms, the dry powder having a lightness of not less than 55 and a chroma of not greater than 18. The method includes an additional step as necessary.

In the present production method, the microorganisms are washed at least once using a liquid having a predetermined osmotic pressure, and thus the lightness and chroma of a dry powder obtained after a powdering step can be adjusted into predetermined ranges.

The step of washing microorganisms which are able to be cultured at least once using a liquid having a predetermined osmotic pressure may be referred to as the "color adjustment processing step" in the present specification. The liquid having a predetermined osmotic pressure used in the washing in the color adjustment processing step may be referred to as a "processing washing liquid" in the present specification. The step of heating and drying the microorganisms collected after the color adjustment processing step to obtain a dry powder of microorganisms having a lightness of not less than 55 and a chroma of not greater than 18 may be referred to as the "powdering step" in the present specification.

In the color adjustment processing step, the microorganisms are washed at least once using a liquid having a lower osmotic pressure than a liquid medium for culturing the microorganisms.

The microorganisms to be subjected to the color adjustment processing step are not particularly limited. The microorganisms can be microorganisms which are able to be cultured and may be any microorganisms obtained from natural collection or after culturing, as long as the microorganisms are able to be cultured. One species of these microorganisms may be used alone, or two or more species of them may be used in combination.

Examples of the microorganisms applicable to the color adjustment processing step may include at least one species selected from the group consisting of microorganisms belonging to fungi, microorganisms of green algae (*Chlorophycea*), microorganisms of *Euglena* algae (*Euglenida*), and microorganisms of SAR. These microorganisms are microorganisms capable of producing mainly oil/lipid and can be preferably applied as oil/lipid-producing microorganisms. Furthermore, examples of such microorganisms may also include microorganisms capable of producing a polysaccharide, an antioxidant, a peptide, an amino acid, a vitamin, or the like, for example, microorganisms capable of producing astaxanthin, such as microalgae including cyanobacteria, red algae, brown algae, green algae, diatoms, and *Eustigmatophyceae*, and in particular, microalgae belonging to the genus *Haematococcus*; and yeasts (e.g., *Phaffia* yeasts); microorganisms capable of producing a polysaccharide including microalgae belonging to the genera, such as *Euglena* and *Prasinococcus*; and filamentous fungi belonging to the genera, such as *Pestalotiopsis* and *Pestalotia*; black yeasts capable of producing pullulan; and yeasts capable of producing mannoprotein. For these microorganisms to be subjected to the color adjustment processing step, the matters described above for the microorganisms with respect to the dry powder are applied as they are.

When the microorganisms subjected to the color adjustment processing step are microorganisms after culturing, the production method according to one embodiment of the present disclosure can further include a culturing step to culture the microorganisms before the color adjustment processing step.

For things such as a culture medium and culture conditions to be applied in the culturing step of the microorganisms, culture media and culture conditions that have been applied to the microorganisms in the art can be applied as they are. In the culturing step, the microorganisms can be cultured and collected from the culture environment after a predetermined culture period. For the method of collecting the microorganisms from the culture environment, a collection method that has been applied to the microorganisms in the art can be applied as it is. For example, microorganisms being cultured in a liquid medium can be collected by a method, such as centrifugation or filtration.

For the temperature condition applied in collecting the microorganisms by centrifugation, for example, a temperature from 5 to 40° C., from 10 to 35° C., or from 15 to 30° C. can be selected. For the centrifugal condition for this procedure, for example, from 600×g to 8000×g, from 800×g to 5000×g, or from 800×g to 3000×g can be selected, and centrifugation under these conditions can be performed for 5 to 10 minutes. The microorganisms can be collected as a residue obtained after removing the supernatant after the centrifugation. The microorganisms after collection can be suspended in the processing washing liquid used in the color adjustment processing step and subjected to the color adjustment processing step.

The processing washing liquid has a lower osmotic pressure than the osmotic pressure of the liquid medium for culturing the microorganisms. The "liquid medium for culturing" means a culture medium typically used in culturing the microorganisms to be subjected to the color adjustment processing step and may be a liquid medium for culturing that has actually been used for the microorganisms to be washed or a liquid medium for culturing that has not been used. The liquid medium for culturing typically has an osmotic pressure equivalent to the growth environment of the microorganisms or suitable for the growth of the microorganisms. The processing washing liquid in a color preparation step has a lower osmotic pressure than the liquid medium for culturing, and thus it is inferred that the microorganisms are exposed to an environment having an osmotic pressure lower than the osmotic pressure suitable for the growth environment, and the processing washing liquid acts on the surfaces of the microbial cells and in some instances on the interior of the microbial cells, resulting in improved lightness and achromatic color of the dry powder, but the production method according to the present disclosure is not limited to this inference.

In subjecting two or more types of microorganisms to the color adjustment processing step, the osmotic pressure of the processing washing liquid can be an osmotic pressure lower than the highest osmotic pressure in comparing an osmotic pressure of each liquid medium used in culturing each type of microorganisms, or the osmotic pressure of the processing washing liquid can be an osmotic pressure lower than the lowest osmotic pressure in the above comparison in terms of providing better lightness and chroma of the resulting dry powder after the drying.

According to one embodiment of the present disclosure, the osmotic pressure of the processing washing liquid used in the color adjustment processing step can be less than 500 mOsm/L, or can be not greater than 450 mOsm/L, not greater than 100 mOsm/L, not greater than 10 mOsm/L, or not greater than 1 mOsm/L according to the type of microorganisms. The osmotic pressure of the processing washing liquid is a value (osmolality) calculated from the concentration of sodium chloride and is a value determined as directed under "2.47 Osmolarity Determination", General Tests, Japanese Pharmacopoeia 17th Edition. The lower limit of the osmotic pressure of the processing washing liquid can be, for example, 0 mOsm/L.

The composition of the processing washing liquid is not particularly limited and any composition that can satisfy the osmotic pressure described above. Examples of the processing washing liquid may include purified water, distilled water, diluted seawater, and physiological saline solution, and the processing washing liquid may be purified water or distilled water.

The washing in the color adjustment processing step means suspending the microorganisms in combination with the processing washing liquid. The amount of the processing washing liquid to be combined with the microorganisms depends on the composition of the processing washing liquid to be used but is basically not limited. The washing can be performed at a temperature condition from 5° C. to 35° C., from 15° C. to 30° C., or at room temperature (25° C.). After suspension, the microorganisms can be separated from the processing washing liquid. For the separation, for example, centrifugation can be applied. The centrifugal condition is a condition typically used in this application, and, for example, from 600×g to 8000×g, from 800×g to 5000×g, or from 800×g to 3000×g can be selected. Specifically, the centrifugation can be applied, for example, using a centrifuge in conditions at 2300×g, at room temperature, and for 5 to 10 minutes.

The washing in the color adjustment processing step is performed at least once and can be performed two or more times, three or more times, or four or more times. In terms of increasing the lightness of the resulting dry powder, the washing can be performed two or more times, or three or more times. The upper limit of the number of washing is not particularly limited. In one embodiment of the present disclosure, the upper limit of the number of the washing can be, for example, not more than six times, not more than five times, not more than four times, or not more than three times in terms of harmony with the colors of other formulation components. In one embodiment of the present disclosure, the washing can be performed one to four times, one to three times, two to four times, or two to three times in terms of obtaining the lightness and chroma that can be harmonized with the colors of other formulation components.

In performing the washing multiple times in the color adjustment processing step, the type of processing washing liquid may be the same or different. In using a different processing washing liquid in each washing, the washing liquids may be liquids having the same osmotic pressure to each other or may be liquids having different osmotic pressures.

The present production method can further include an autoclaving step. The autoclaving in the present specification means a heat treatment under wet normal or increased pressure, and the autoclaving step means a step of performing such autoclaving. Typically, in using a microbial dry powder as a component in a product, such as a food product, sterilization may be performed before or after powdering. The autoclaving is performed under conditions typically used for sterilizing microorganisms, and, for example, conditions of raising the temperature from normal temperature to 121° C. and then maintaining at 121° C. for 20 minutes can be applied. Other conditions applied for sterilization purposes may be applied as the conditions for the autoclaving. In subjecting the microorganisms to the autoclaving, the microorganisms in the culture medium may be subjected to the autoclaving, and the microorganisms separated from the culture medium may be autoclaved as they are or after suspended in another solution. The microbial dry powder obtained through the autoclaving step tends to be colored, that is, tends to have low lightness and high chroma, but applying the production method according to the present disclosure can provide a dry powder with high lightness and low chroma.

The autoclaving step is performed at least once and can be performed, for example, before or after the washing in the color adjustment processing step. In one embodiment of the present disclosure, the autoclaving step can be performed after the washing in terms of efficiently reducing the chroma.

The present production method can further include a collecting step to collect the microorganisms after the color adjustment processing step or after the autoclaving step. A method of collecting microorganisms typically used for this purpose can be applied to collect the microorganisms. For example, microorganisms suspended in the processing washing liquid can be collected by a technique, such as centrifugation or filtration.

For the temperature condition applied in collecting the microorganisms by centrifugation, for example, a temperature from 5 to 40° C., from 10 to 35° C., or from 15 to 30° C. can be selected. For the centrifugal condition for this procedure, for example, from 600×g to 8000×g, from 800×g to 5000×g, or from 800×g to 3000×g can be selected, and centrifugation under these conditions can be performed for 5 to 10 minutes. In this case, the microorganisms can be collected as a residue obtained after removing the supernatant after the centrifugation. The microorganisms after collection can be subjected to other treatments in a state of being collected as a residue or after further being suspended in another liquid.

In the powdering step, the microorganisms after washing are heat-dried to obtain a dry powder of microorganisms having a lightness of not less than 55 and a chroma of not greater than 18. The method of heating and drying applied in the powdering step is a method of heating and drying typically applied to powder microorganisms and can be performed, for example, at a temperature from 60° C. to 150° C., from 70° C. to 120° C., or from 80° C. to 100° C. for 2 hours to 6 hours or 3 hours to 4 hours under a windless or blowing condition. Alternatively, in one embodiment of the present disclosure, a method such as drying under reduced pressure and lyophilisation may be used.

The resulting dry powder can have a water content obtained under the drying conditions described above. The water content of the dry powder in one embodiment of the present disclosure may be not more than 15 wt. %, for example, not more than 10 wt. %. The water content of the dry powder can be measured as directed under "2.48 Water Determination (Karl Fischer Method)", General Tests, Japanese Pharmacopoeia 17th Edition.

The method of producing a dry powder of microorganisms according to an embodiment of the present disclosure can include an additional step after the powdering step. Examples of the additional optional step that can be added may include a step of collecting the dry powder and an autoclaving step to autoclave the collected dry powder.

The dry powder according to the present disclosure can retain a useful component contained in microorganisms as a dry powder. Thus, the microbial dry powder and the method of producing the microbial dry powder according to the present disclosure are particularly useful in such a case as utilizing, storing, or applying a useful microbial-derived component contained in the microbial dry powder. The dry powder according to the present disclosure may be reconstituted in combination with a liquid carrier, such as water, in a suitable weight ratio to form a liquid reconstituted composition containing a microbial-derived component. The resulting reconstituted composition can be utilized as a particular product or as a component in a particular product.

Applications

One embodiment of the present disclosure can provide a powder product containing the dry powder of microorganisms described above.

The microbial dry powder according to the present disclosure has a predetermined lightness and a predetermined chroma and is a bright and achromatic microbial dry powder, and thus the present powder product can contain the dry powder of microorganisms without impairing the overall color impression of the product.

Examples of the powder product containing the dry powder of microorganisms according to the present disclosure may include various products, such as food and beverage products, personal care products, pharmaceuticals, quasi drugs, and animal feeds.

In addition, the powder product according to the present disclosure may be further mixed with a liquid carrier, such as water, in a suitable weight ratio to form a liquid product, or a liquid product is formed and then may be further solidified to form a solid product.

Examples of the food and beverage products may include frozen desserts, such as ice creams, ice milks, and ice confectionery; beverages, such as milk drinks, lactic acid bacteria beverages, soft drinks, carbonated drinks, sports drinks, and supplement drinks; desserts, such as puddings, jellies, Bavarian creams, and yogurts; confectionery, such as chewing gums, chocolates, soft candies, hard biscuits, and cookies; soups; meat-processed products, such as hams, sausages, and roast pork; seafood paste products, such as fish meat, fish sausages, minced fish meat, and steamed fish cake (kamaboko); and dairy oil and fat products, such as butter, margarine, and cheese.

Examples of the personal care product may include skin care cosmetics, such as lotions, milky lotions, and creams; cosmetic products, such as lipsticks, sunscreen cosmetics, and make-up cosmetics; and bar soaps, liquid soaps, shampoos, and conditioners. Examples of the pharmaceuticals may include various tablets, capsules, drinks, troches, and mouthwashes.

Examples of the quasi drug products may include dentifrices, mouth fresheners, and breath deodorizers. Examples of the animal feeds may include various pet foods, such as cat foods and dog foods; food for ornamental fish or farmed fish; and food for domestic animals, such as poultry.

The powder product according to the present disclosure can contain the microbial dry powder described above in a formulation amount according to the type, purpose, or the like of the product, and the formulation amount of the microbial dry powder in 100 wt. % of the product is not particularly limited and can be appropriately selected from a range typically from 0.01 to 10 wt. % or other ranges.

The powder product according to the present disclosure can contain a carrier component. The carrier component may be either a fixed component or a liquid component and can be appropriately selected according to the application of the product from carriers, such as pharmaceutically acceptable carriers, carriers acceptable as food and beverage products, cosmetically acceptable carriers, and carriers acceptable as animal feeds.

The powder product according to the present disclosure can contain as necessary an additive of various types typically used in various applications. Examples of various types of additive include diluents, binders, preservatives, stabilizers, disintegrators, lubricants, and flavoring agents.

The powder product according to the present disclosure can be obtained by a production method including obtaining the dry powder described above and blending the resulting dry powder into a carrier component to obtain a powder product. The present production method may further include a step of blending an additive of various types into the dry powder.

The microbial dry powder according to the present disclosure has a predetermined lightness and a predetermined chroma and is a bright and achromatic microbial dry powder, and thus this can provide the powder product containing a useful component that the microorganisms have without impairing the overall color impression of the product.

The method of producing a powder product can further include a step of formulating the dry powder. Examples of the method of formulating may include liquefying, pelletizing, encapsulating, and tableting. The treatments and methods required for these formulations are well known to those skilled in the art.

The powder product according to the present disclosure can be used in an amount or an effective amount according to each application. For example, in pharmaceutical applications, the amount used or effective amount of the powder product can be appropriately set according to the type of the microbial-derived component, the mode of administration, the purpose of administration, the condition of the subject receiving the powder product, such as, for example, gender, age, and body weight.

In one embodiment of the present disclosure, for example, in orally administering a fatty acid, for example, docosahexaenoic acid (DHA), as the microbial-derived component to an adult, the effective amount can be appropriately adjusted in a range from 0.01 mg to 10 g, preferably from 0.1 mg to 2 g, and more preferably from 1 mg to 200 mg, per day as the total amount of the DHA. In addition, in peroral administration, the effective amount can be appropriately adjusted in a range from 0.001 mg to 1 g, preferably from 0.01 mg to 200 mg, and more preferably from 0.1 mg to 100 mg, per day as the total amount of the DHA as a structured lipid.

The dry powder according to the present disclosure retains a useful component contained in microorganisms, that is a microbial-derived component and thus is useful for such a purpose as storing the microbial-derived component over a predetermined period.

A method of producing a microbial-derived component-containing composition according to one embodiment of the present disclosure includes preparing the dry powder of microorganisms described above and obtaining a microbial-derived component-containing composition from the prepared dry powder. In the present specification, the step of preparing the dry powder of microorganisms described above may be referred to simply as the dry powder obtaining step, and the step of obtaining the microbial-derived component-containing composition from the prepared dry powder may be referred to simply as the separation step.

The present production method can provide a useful component in microorganisms as a microbial-derived component-containing composition from the dry powder of microorganisms described above.

In the dry powder obtaining step, a dry powder of microorganisms is obtained by the method of producing a dry powder of microorganisms described above. The matters described for the method of producing the dry powder can be applied as they are.

In the separation step, the microbial-derived component is separated from the dry powder obtained in the dry powder obtaining step, and a microbial-derived component-containing composition is obtained. The method of separating a microbial-derived component can be selected physically or chemically as appropriate according to the type of microbial-derived component to be separated. Examples of the method of separation may include a method of extracting a microbial component using an extraction solvent or the like, and a method of separating using chromatography, such as gas chromatography.

The microbial-derived component to be obtained is not particularly limited, and examples of the microbial-derived component may include amino acids, proteins, lipids, and vitamins as described above. The microbial-derived component-containing composition means a composition containing a microbial-derived component alone or a plurality of microbial-derived components in combination and containing an additional carrier component as necessary. The carrier component that may be contained in the microbial-derived component-containing composition may be a solid component or a liquid component.

For example, oil/lipid-producing microorganisms when used as the microorganisms can provide oil/lipid containing a microbial-derived component that is a microbial oil/lipid. The microbial oil/lipid is a fatty acid-containing composition that may contain a single or a plurality of fatty acids. The resulting fatty acid-containing composition contains a useful fatty acid component contained in microorganisms and thus can be used in various applications based on the functionality of the fatty acid, such as, for example, food and beverage products, pharmaceuticals, quasi drugs, personal care products, and animal feeds.

EXAMPLES

Hereinafter, the present disclosure will be described in detail with reference to examples.

However, the present invention is not limited in any manner by these examples. Unless otherwise noted, "part" or "%" is on a mass basis.

Examples 1 to 6

(1) Culture of Microorganisms

"SEK 704 AB973560 strain" (Aquat. Microb. Ecol., 2015, Vol. 74, pp. 187-204), which is a related species of AR2-1 AB810959 of the genus *Thraustochytrium* sp., of an unidentified family *Thraustochytrid*, was obtained from Biotechnology Center, National Institute of Technology and Evaluation and suspended in 50% artificial seawater described below, and then 0.1 mL of this microbial suspension was inoculated in a 500-mL pleated shaking flask containing 100 mL of a liquid medium (469 mOsm/L) for *Thraustochytrid*. A culture vessel, Bio-Shaker BR-300LF (Taitec Corporation), was used to shake the flask at 28° C. at 120 rpm for 2 to 3 days. The resulting cell suspension was used as a pre-culture liquid to inoculate into a jar fermenter.

TABLE 1

| Liquid medium for Thraustochytrid (1 liter) | |
|---|---|
| Glycerol | 30 g |
| Yeast extract | 10 g |
| NaCl | 15 g |
| KCl | 0.35 g |
| $MgCl_2 \cdot 6H_2O$ | 5.4 g |
| $MgSO_4 \cdot 7H_2O$ | 2-7 g |
| $CaCl_2 \cdot 2H_2O$ | 0.5 g |
| Vitamin E solution* | 1.0 mL |
| Metal salt solution** | 1.0 mL |
| Deionized water | Remainder |

TABLE 2

Vitamin solution (1 liter)

| | |
|---|---|
| Thiamine hydrochloride | 9.75 g |
| Calcium pantothenate | 3.33 g |
| Cyanocobalamin | 0.16 g |
| Biotin | 3.58 g |
| Deionized water | Remainder |

TABLE 3

Metal salt solution (1 liter)

| | |
|---|---|
| Citric acid | 46.8 g |
| $FeSO_4 \cdot 7H_2O$ | 10.3 g |
| $MnCl_2 \cdot 4H_2O$ | 3.1 g |
| $ZnSO_4 \cdot 7H_2O$ | 9.3 g |
| $CoCl_2 \cdot 6H_2O$ | 0.04 g |
| $NaMoO_4 \cdot 2H_2O$ | 0.04 g |
| $CuSO_4 \cdot 5H_2O$ | 2.07 g |
| $NiSO_4 \cdot 6H_2O$ | 2.07 g |
| Deionized water | Remainder |

A medium containing 30 g of glucose, 10 g of yeast extract, 15 g of NaCl, 0.35 g of KCl, 5.4 g of $MgCl_2 \cdot 6H_2O$, 2.7 g of $MgSO_4 \cdot 7H_2O$, 0.5 g of $CaCl_2 \cdot 2H_2O$, 1.0 mL of the vitamin solution, and 1.0 mL of the metal salt solution was prepared to be 1.0 L, and 0.5 L of this medium was placed into a 1-L capacity fermenter, and 1% amount (v/v) of the pre-culture liquid was inoculated in that medium.

Culture was performed in conditions of a culture temperature of 20° C., 26° C., or 32° C., a stirring speed of 600 rpm, an air flow rate of 1 vvm, a gauge pressure in the fermenter of 0 MPa, and a pH of 6.8±0.2 for 1 to 4 days. During the culture, when large amounts of foaming occurred, a foam inhibitor was added as appropriate. Antifoam, such as soybean oil and KM-72 F, can be used.

(2) Color Adjustment Processing Step and Powdering Step

To a weighed 50-mL centrifuge tube, 40 mL of cultured cell suspension after culturing was collected. The microorganisms collected in the centrifuge tubes were each designated as Microbial Samples A to F. Each microbial sample was subjected to each step in the order shown in Table 5.

In Table 5, processing is shown in a time series from left to right in the table, and the check mark means that the processing at the stage indicated in the table was performed. In Table 5, "–" means that the processing at the stage shown in the table was not performed. In Table 5, "*" indicates whether the processing at the stage shown in the table was performed is unknown. In Table 5, "AC" means the autoclaving step. In Table 5, "DW" means purified water.

Centrifugation Step

The centrifuge tube containing the microbial sample was subjected to centrifugation at 5000 rpm (2300×g) at room temperature for 5 minutes using a high speed refrigerated micro centrifuge. A high speed refrigerated micro centrifuge "MX-300" (Tomy Seiko Co., Ltd.) was used.

When the powdering step after the centrifugation step was performed, the supernatant was removed by centrifugation, and the microbial sample obtained as the residue was subsequently used in the powdering step.

Washing Step

The supernatant was discarded from the centrifuge tube containing the microbial sample after the centrifugation step, and 40 mL of the processing washing liquid was added to the residue after discarding the supernatant, and the residue was lightly suspended. When the washing step was repeated, the microbial sample was suspended in the processing washing liquid, then the supernatant was removed by centrifugation in the same conditions as in the centrifugation step, and the processing washing liquid was added to the residue. The processing washing liquid used in Examples 1 to 6 was purified water (osmotic pressure: 0 mOsm/L).

Autoclaving Step

The centrifuge tube containing the microbial sample was placed in an autoclave (LSX-700, Tomy Seiko Co., Ltd.), the temperature was increased to 121° C., and autoclaving was performed for a holding time of 20 minutes after the temperature reached 121° C.

When the autoclaving step was performed after the centrifugation step, autoclaving was performed on the microbial sample as a residue after removal of the supernatant, and when the autoclaving step was performed subsequently after the washing step, autoclaving was performed on the microbial sample suspended in the processing washing liquid.

Powdering Step

The centrifuge tube containing the microbial sample is heat-dried at 105° C. for 3 hours, and a dry powder is obtained. A low-temperature blow dryer (Tokyo Rikakikai Co., Ltd.) was used for the heating and drying. The water content of the resulting dry powder is not more than 15 wt. %.

Measurement

From 0.5 g to 1.0 g of the dry powder of microorganisms was placed in a transparent bag ("Unpack (trade mark)" Type 0.04 B-4, length under the fastener of 85 mm×bag width of 60 mm×thickness of 0.04 mm, Seisan Nipponsha Ltd.). Particles of the dry powder of microorganisms in large masses of not less than 1 mm were crushed to homogenize. Subsequently, the dry powder was collected in the bag to form a layer with a thickness of about 1 mm and used as a measurement sample. The measuring head part of the chroma meter CR-300 was applied perpendicular to the sample from above the bag, and the chromatic color difference was measured.

Before measuring the sample, calibration by calibration channel 00 with a white calibration plate was performed. In addition, the measurement was performed under room temperature (from 20 to 25° C.) and a relative humidity from 20% to 30%. The results are shown in Table 5.

Comparative Examples 1 to 5

The microorganisms collected in the centrifuge tubes after culturing were each designated as Microbial Samples G to H, and each step was performed in the order shown in Table 5 in the same manner as in Examples 1 to 6. The lightness and chroma of the resulting dry powder was measured in the same manner as in Examples 1 to 6. The results are shown in Table 5.

However, in Comparative Examples 3 and 4, a solution of a Herbst formulation shown in Table 4 and purified water with a volume ratio of 1:1 (hereinafter, referred to as a "50% artificial seawater") was used as the processing washing liquid instead of purified water. The osmotic pressure of this 50% artificial seawater is 469 mOsm/L, and this osmotic pressure is the same value as the osmotic pressure of the liquid medium for *Thraustochytrid*.

TABLE 4

Herbst formulation (1 liter)

| | |
|---|---|
| NaCl | 30 g |
| KCl | 0.7 g |
| $MgCl_2 \cdot 6H_2O$ | 10.8 g |
| $MgSO_4 \cdot 7H_2O$ | 5.4 g |
| $CaCl_2 \cdot 2H_2O$ | 1.0 g |
| Deionized water | Remainder |

In Comparative Example 5, a liquid containing 3 wt. % of glycerol, 1 wt. % of yeast extract, and the 50% artificial seawater (hereinafter, referred to as a "medium component") was used as the processing washing liquid instead of purified water. The osmotic pressure of this medium component was 469 mOsm/L.

Comparative Example 6

A powder of *Schizochytrium* "Bio-Chromis Powder" (Chlorella Industry Co., Ltd.) was obtained and designated as Microbial Sample L, and in the same manner as in Example 1, the lightness and chroma were measured in the same manner as in Example 1. The results are shown in Table 5. In Table 5, "*" means that information is not known.

washing liquid, increasing the number of washing allows the lightness and chroma to be adjusted. Especially for the lightness, it was found that increasing the number of washing allows the resulting dry powder to exhibit higher lightness. When the dry powders of Microbial Samples A to F were stored for one month, the lightness and chroma remained unchanged.

It is understood that the dry powder according to the present disclosure is a dry powder of microorganisms, the dry powder with superior processing suitability and excellent utility as a component of various products as described above.

In addition, it can be understood that use of such a dry powder can provide a powder product containing a microbial-derived component and excellent in utility.

TABLE 5

| | Microbial sample | AC | Centrifugation | Washing | Processing washing liquid | Centrifugation | AC | Centrifugation | Lightness | Chroma | Hue |
|---|---|---|---|---|---|---|---|---|---|---|---|
| Example 1 | A | — | ✓ | ✓ | DW | ✓ | ✓ | — | 58.6 | 13.1 | 72.8 |
| Example 2 | B | ✓ | ✓ | ✓ | DW | ✓ | — | — | 59.3 | 13.0 | 74.9 |
| Example 3 | C | — | ✓ | ✓ | DW | — | ✓ | — | 57.8 | 14.9 | 72.5 |
| Example 4 | D | — | ✓ | Twice | DW | ✓ | ✓ | — | 62.2 | 14.3 | 73.3 |
| Example 5 | E | — | ✓ | 3 times | DW | ✓ | ✓ | — | 65.4 | 13.9 | 76.6 |
| Example 6 | F | — | ✓ | 4 times | DW | ✓ | ✓ | — | 66.9 | 16.3 | 76.8 |
| Comparative Example 1 | G | ✓ | ✓ | — | — | — | — | — | 58.9 | 19.3 | 74.9 |
| Comparative Example 2 | H | — | ✓ | — | — | — | ✓ | — | 54.8 | 15.7 | 71.0 |
| Comparative Example 3 | I | — | ✓ | ✓ | 50% Artificial seawater | ✓ | ✓ | — | 52.8 | 16.2 | 71.6 |
| Comparative Example 4 | J | — | ✓ | ✓ | 50% Artificial seawater | — | ✓ | ✓ | 58.2 | 18.7 | 72.8 |
| Comparative Example 5 | K | — | ✓ | ✓ | Medium component | — | ✓ | ✓ | 52.7 | 17.7 | 68.5 |
| Comparative Example 6 | L | * | * | * | * | * | * | * | 71.2 | 37.2 | 80.9 |

As shown in Table 5, it was found that Microbial Samples A to F washed using purified water as the processing washing liquid had good balance of lightness and chroma and, in particular, significantly reduced chroma when these samples were formed into dry powders compared with Microbial Samples G to K which were not washed or washed using the processing washing liquid with the same osmotic pressure as the osmotic pressure of the medium component of 469 mOsm/L. Microbial Samples A to F had relatively high lightness and chroma close to achromatic color as dry powders, and thus it is clear that each of these samples is easy to use as a component of a powder product and excellent in processing suitability.

In contrast, Microbial Sample L of Comparative Example 6, which is a commercial product of a dry powder of microorganisms, had a high lightness of greater than 70 but on the other hand also had a significantly high chroma of 37.2, having a color intensified in the yellow direction and vivid. If Microbial Sample L is mixed as a component with other formulation components in a powder product, the color intensified in the yellow direction and vivid can impair a sense of unity with other formulation components.

In addition, as shown in Examples 1, and 4 to 6, it is understood that in using purified water with an osmotic pressure of not greater than 450 mOsm/L as the processing

The invention claimed is:

1. A dry powder of microorganisms having a lightness of not less than 55 and a chroma not greater than 18, wherein the microorganisms are at least one species in the clade *Stramenopiles* or in the class *Labyrinthulea*.

2. The dry powder according to claim 1, having a lightness of not less than 58 and a chroma not greater than 18.

3. The dry powder according to claim 1, having a lightness of not less than 58 and a chroma not greater than 17.

4. The dry powder according to claim 1, having a lightness of not less than 60 and a chroma not greater than 15.

5. The dry powder according to claim 1, wherein the microorganisms are oil/lipid-producing microorganisms.

6. A dry powder production method of producing the dry powder of microorganisms of claim 1, the method comprising:
  a) washing the microorganisms at least once using a liquid having a lower osmotic pressure than a liquid medium for culturing the microorganisms; and
  b) heating and drying of the microorganisms after the washing to obtain a dry powder of microorganisms, the dry powder having a lightness of not less than 55 and a chroma of not greater than 18.

7. The production method according to claim 6, further comprising an autoclaving step.

8. The production method according to claim 7, comprising the autoclaving step after the washing.

9. The production method according to claim 6, wherein the washing is performed from one to three times.

10. The production method according to claim 6, wherein the method further comprises a culturing step for culturing the microorganisms before the washing.

11. The production method according to claim 6, wherein the microorganisms are oil/lipid-producing microorganisms.

12. A powder product comprising the dry powder described in claim 1.

* * * * *